(12) United States Patent
Nawata et al.

(10) Patent No.: US 7,549,747 B2
(45) Date of Patent: Jun. 23, 2009

(54) OPHTHALMOLOGIC IMAGING SYSTEM

(75) Inventors: Hiroshi Nawata, Tokyo (JP); Naoki Kaneda, Tokyo (JP); Shigeki Yagioka, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 20 days.

(21) Appl. No.: 11/833,071

(22) Filed: Aug. 2, 2007

(65) Prior Publication Data
US 2008/0030684 A1 Feb. 7, 2008

(30) Foreign Application Priority Data
Aug. 2, 2006 (JP) ............................... 2006-210877

(51) Int. Cl.
*A61B 3/14* (2006.01)
*A61B 3/10* (2006.01)
(52) U.S. Cl. .................. 351/206; 351/205; 351/221
(58) Field of Classification Search ................. 351/200, 351/204–206, 210, 212, 221
See application file for complete search history.

(56) References Cited

U.S. PATENT DOCUMENTS 5,680,196 A * 10/1997 Masuda ...................... 351/208
7,370,966 B2 * 5/2008 Fukuma et al. ............. 351/205

FOREIGN PATENT DOCUMENTS

JP 2005-006894 1/2007

* cited by examiner

*Primary Examiner*—Mohammed Hasan
(74) *Attorney, Agent, or Firm*—Edwards Angell Palmer & Dodge LLP

(57) ABSTRACT

An ophthalmologic imaging system comprises: a retinal camera having an illuminating optical system configured to project an illuminating light onto fundus oculi of a subject and an imaging optical system including an imaging part configured to receive the fundus reflection light of the illuminating light and output an imaging signal; and a computer having a package separate from the retinal camera, communicably connected to the retinal camera, and having a display configured to display a fundus oculi image based on the imaging signal, wherein: the retinal camera comprises an operation part; and the computer comprises a controller configured to instruct the display to display information based on an operation signal transmitted from the retinal camera in response to an operation by the operation part.

7 Claims, 9 Drawing Sheets

| TYPES OF IMAGING METHOD | FILTER 8 | FILTER 1 | FILTER 2 | FILTER 3 | FILTER 4 | FILTER 5 | ... |
|---|---|---|---|---|---|---|---|
| | COLOR | FA | ICG | AUTO FLUORESCENCE | GREEN | BULE | |
| PROCEDURE | FOR COLOR | FOR B/W-1 | FOR B/W-2 | FOR B/W-2 | FOR B/W-1 | FOR B/W-1 | |

| PROCEDURE | FOR COLOR | FOR B/W-1 | FOR B/W-2 | ... |
|---|---|---|---|---|
| IMAGING DEVICE | IMAGING DEVICE-A | IMAGING DEVICE-B | IMAGING DEVICE-B | ... |
| SETTING | #1 | #2 | #3 | ... |

| SETTING | IMAGING DEVICE-A #1 | IMAGING DEVICE-B #1 | IMAGING DEVICE-B #2 | ... |
|---|---|---|---|---|
| IMAGING SENSITIVITY | ISO500 | Gain 12 | Gain 18 | ... |
| FILM VALID PIXELS | 2000×1500 | 1600×1200 | 1600×1200 | ... |
| ... | | | | |

FIG. 12

| ID. | First Name | Last Name | DB# | Color | FA | ICG | Green | BLUE | AutoFl… |
|---|---|---|---|---|---|---|---|---|---|
| 222-22-2222 | AAAA | BBBB | 0 | --:--:-- | 00:04:40 | 00:03:53 | --:--:-- | --:--:-- | --:--:-- |
| 000-00-0000 | TOPCON | TEST | 0 | --:--:-- | 00:09:46 | 00:04:27 | --:--:-- | --:--:-- | --:--:-- |
| 2006-07-07 | TEST | DXCapture | 0 | --:--:-- | 00:04:57 | 00:04:08 | --:--:-- | --:--:-- | --:--:-- |

2000

OPHTHALMOLOGIC IMAGING SYSTEM

BACKGROUND OF THE INVENTION

1. Field of the Invention

The present invention relates to an ophthalmologic imaging system configured to capture an image of an eye.

2. Description of the Related Art

In recent years, digitization of medical images has made progress. Particularly in the ophthalmic field, the merit of digitization is believed to be relatively significant, as well as in the radiographic image field, because of the property of utilizing multiple images in diagnosis.

An ophthalmologic imaging system is generally configured by connecting an ophthalmologic imaging device to a computer. As an ophthalmologic imaging device, a retinal camera, a slit lamp, an OCT (Optical Coherence Tomography), and so on are known. In addition, as a computer to be connected to the ophthalmologic imaging device, those employed in the operation of setting up the ophthalmologic imaging device, those for storing image data of captured images, and so on are employed.

JP Patent laid-open No. 2005-6894 discloses an ophthalmologic imaging system in the form of connecting a retinal camera to a computer for setup. This ophthalmologic imaging system is configured to perform the following setting operations of the retinal camera on the computer side and to unify the setting contents on the computer side: (1) setting of imaging types (color imaging, visible fluorescence imaging, infrared fluorescence imaging, and so on); (2) setting of imaging sensitivity of an image pick-up element (CCD); (3) setting of resolution of captured images; (4) setting of color images/monochrome images; (5) setting of illumination light volume; (6) setting of the compression rate of image data; and (7) setting of imaging interval.

Such a conventional ophthalmologic imaging system is effective in the management of imaging information, but it is feared that there is a problem in terms of efficiency of imaging as described below.

When operating the imaging system, an examiner is located facing a subject across the ophthalmologic imaging device. The computer is, as shown for example in FIG. 2 of JP Patent laid-open No. 2005-6894, generally placed alongside the examiner facing the subject. The examiner performs imaging in a position facing the subject—that is, the ophthalmologic imaging device. A captured image is displayed on a display unit of the ophthalmologic imaging device or the computer.

When terminating imaging of that subject and shifting to imaging of the next subject, or when implementing another type of imaging on the same subject, the examiner needs to change his/her position to face not the ophthalmologic imaging device but the computer, and to change the setting of the ophthalmologic imaging device by operating a keyboard and/or a mouse. In a conventional ophthalmologic imaging system, the examiner performs such operations for each setting change, so that it is difficult to improve the efficiency of imaging work.

In particular, when performing imaging of a plurality of subjects consecutively (such a case occurs on a daily basis), the examiner needs to frequently change settings of the ophthalmologic imaging device, so that the efficiency of imaging may decrease significantly.

SUMMARY OF THE INVENTION

The present invention provides an ophthalmologic imaging system comprising: a retinal camera having an illuminating optical system configured to project an illuminating light onto fundus oculi of a subject and an imaging optical system including an imaging part configured to receive the fundus reflection light of the illuminating light and output an imaging signal; and a computer having a package separate from the retinal camera, communicably connected to the retinal camera, and having a display configured to display a fundus oculi image based on the imaging signal output by the imaging part, wherein: the retinal camera comprises an operation part; and the computer comprises a controller configured to instruct the display to display information based on an operation signal transmitted from the retinal camera in response to an operation by the operation part.

BRIEF DESCRIPTION OF THE DRAWINGS

FIG. 7 is a schematic diagram showing one example of the pattern of relating information stored in the computer of the preferred embodiment of the ophthalmologic imaging system according to the present invention.

FIG. 8 is a schematic diagram showing one example of the pattern of relating information stored in the computer of the preferred embodiment of the ophthalmologic imaging system according to the present invention.

FIG. 9 is a schematic diagram showing one example of the pattern of relating information stored in the computer of the preferred embodiment of the ophthalmologic imaging system according to the present invention.

FIG. 12 is a schematic diagram showing one example of the screen displayed in the preferred embodiment of the ophthalmologic image system according to the present invention.

DETAILED DESCRIPTION OF THE PREFERRED EMBODIMENTS

Figure 1:
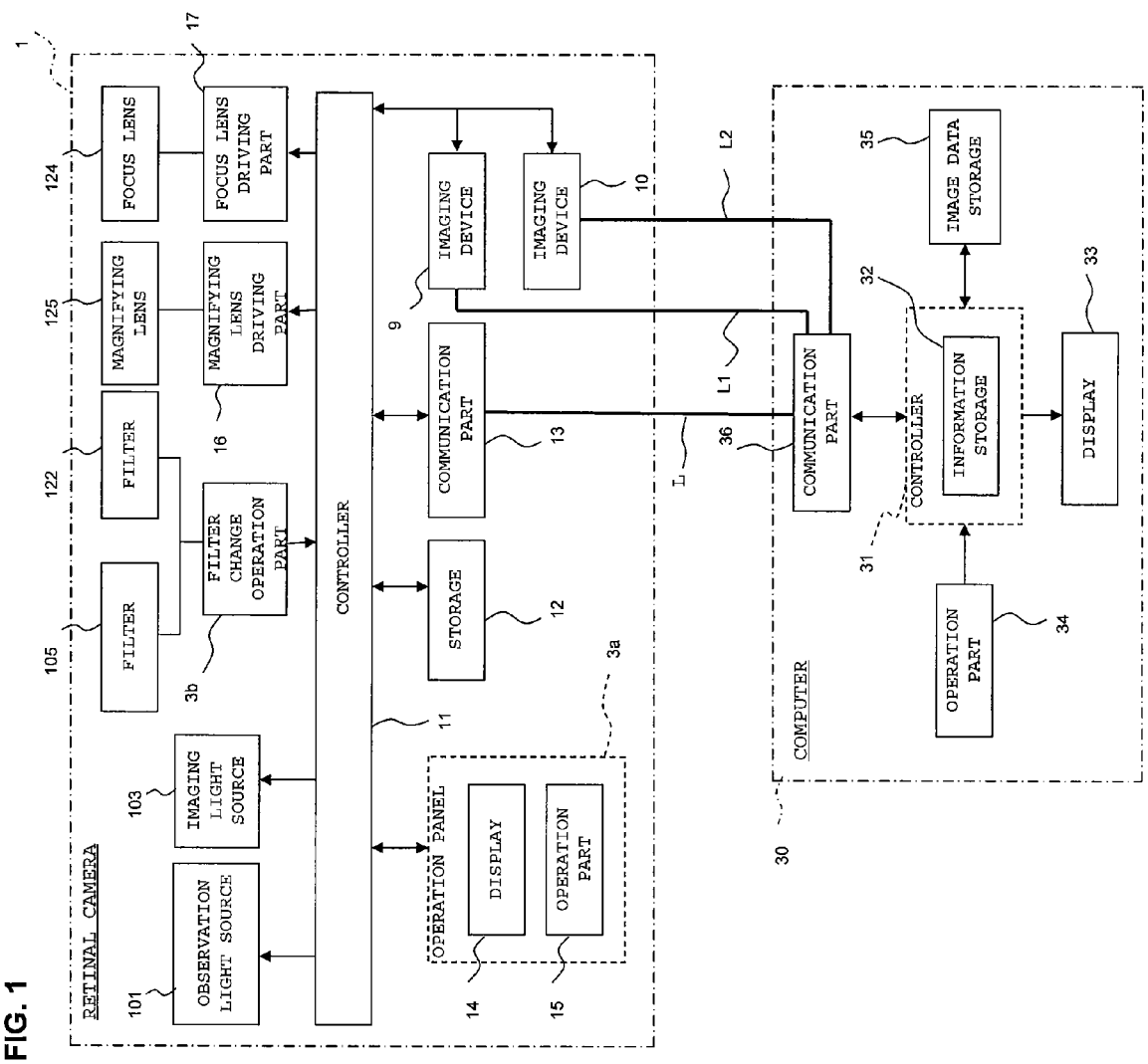
FIG. 1 is a schematic block diagram showing one example of the entire configuration of a preferred embodiment of an ophthalmologic imaging system according to the present invention.

A preferred embodiment of the ophthalmologic imaging system according to the present invention will be described in detail referring to the drawings.

System Configuration

One example of the entire configuration of the ophthalmologic imaging system according to this embodiment is shown in FIG. 1. The ophthalmologic imaging system shown in FIG. 1 comprises a retinal camera 1 for imaging a fundus oculi image, and a computer 30. The retinal camera 1 and the computer 30 have separate packages. Hereinafter, the configurations of the retinal camera 1 and the computer 30 will be each described.

Configuration of Retinal Camera

Figure 2:
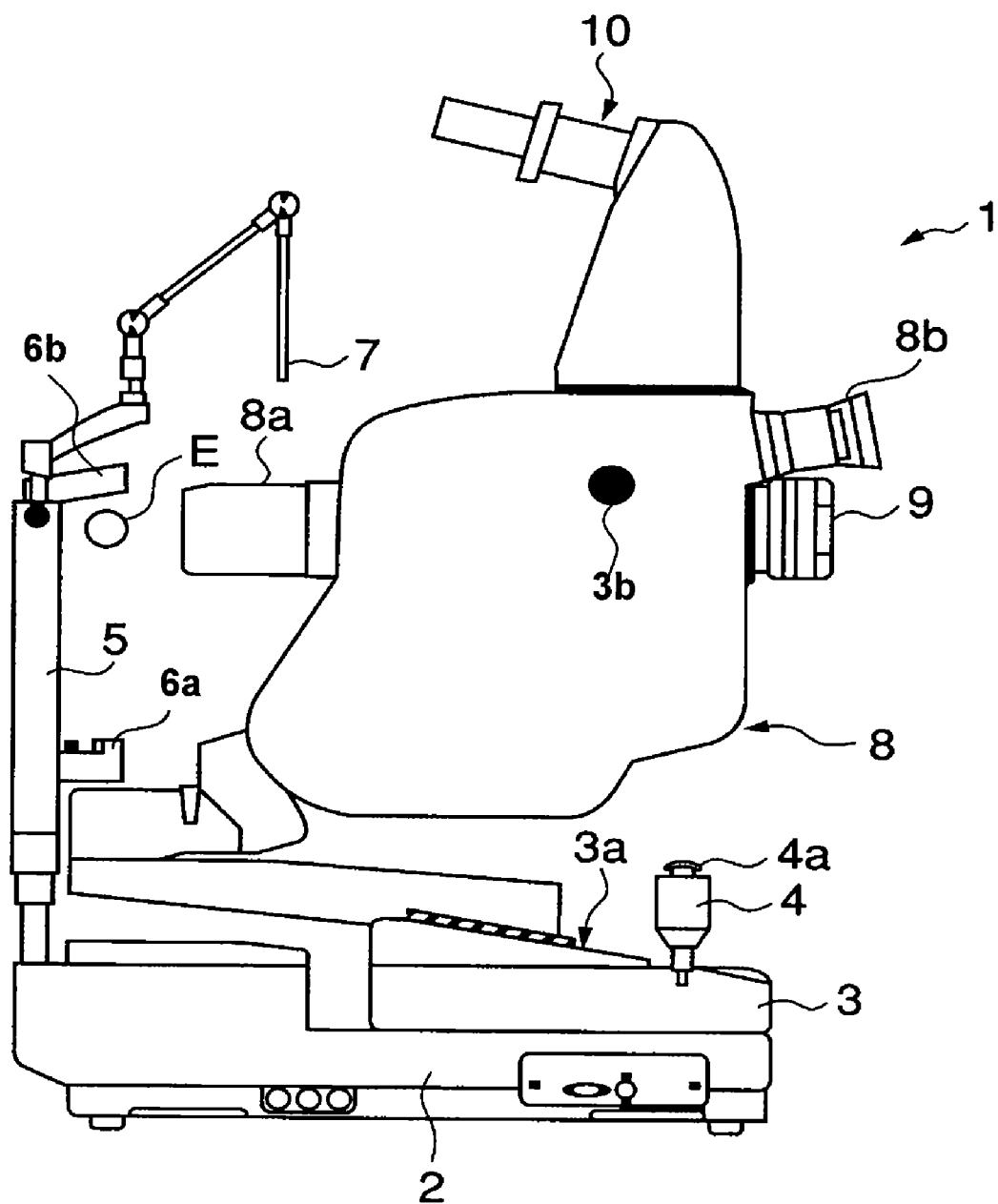
FIG. 2 is a schematic side view showing one example of the structural appearance of a retinal camera of the preferred embodiment of the ophthalmologic imaging system according to the present invention.
Figure 3:
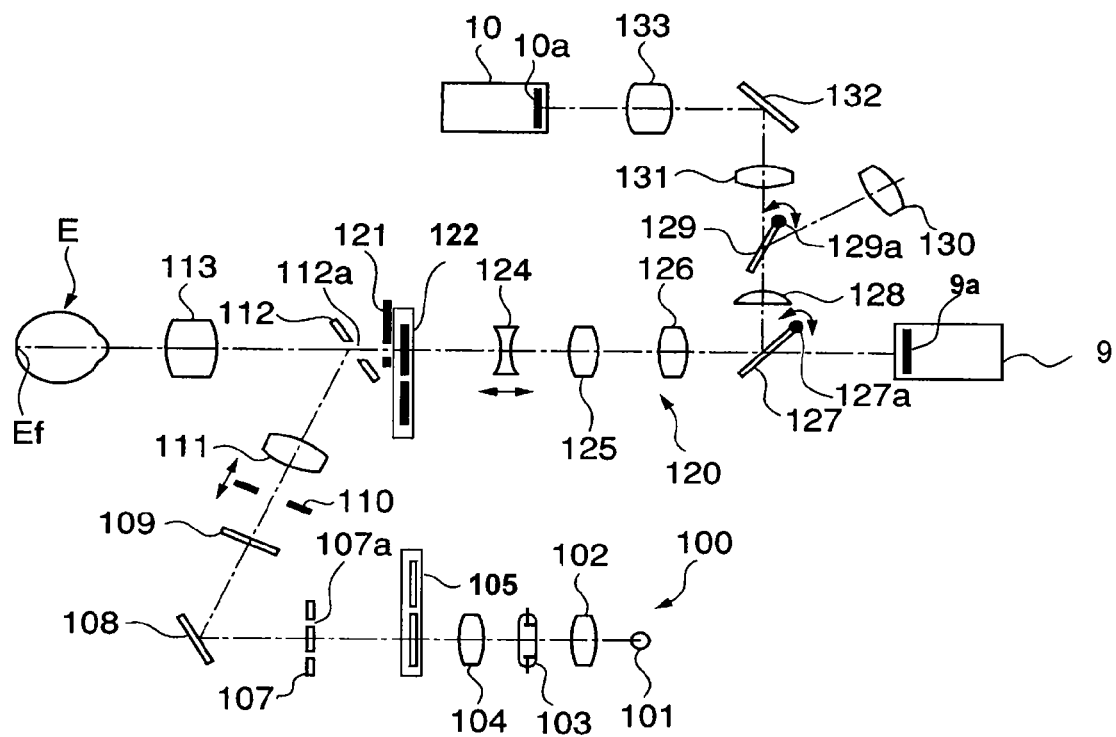
FIG. 3 is a schematic side view showing one example of the configuration of an optical system of the retinal camera of the preferred embodiment of the ophthalmologic imaging system according to the present invention.
Figure 4:
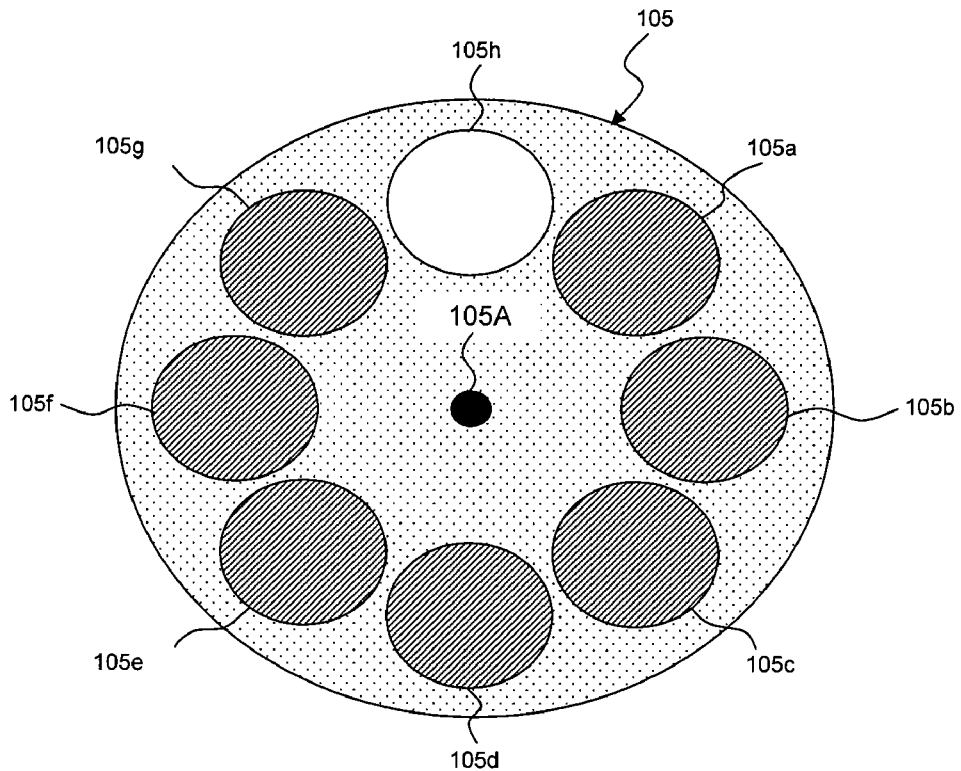
FIG. 4 is a schematic side view showing one example of the configuration of the optical system of the retinal camera of the preferred embodiment of the ophthalmologic imaging system according to the present invention.
Figure 5:
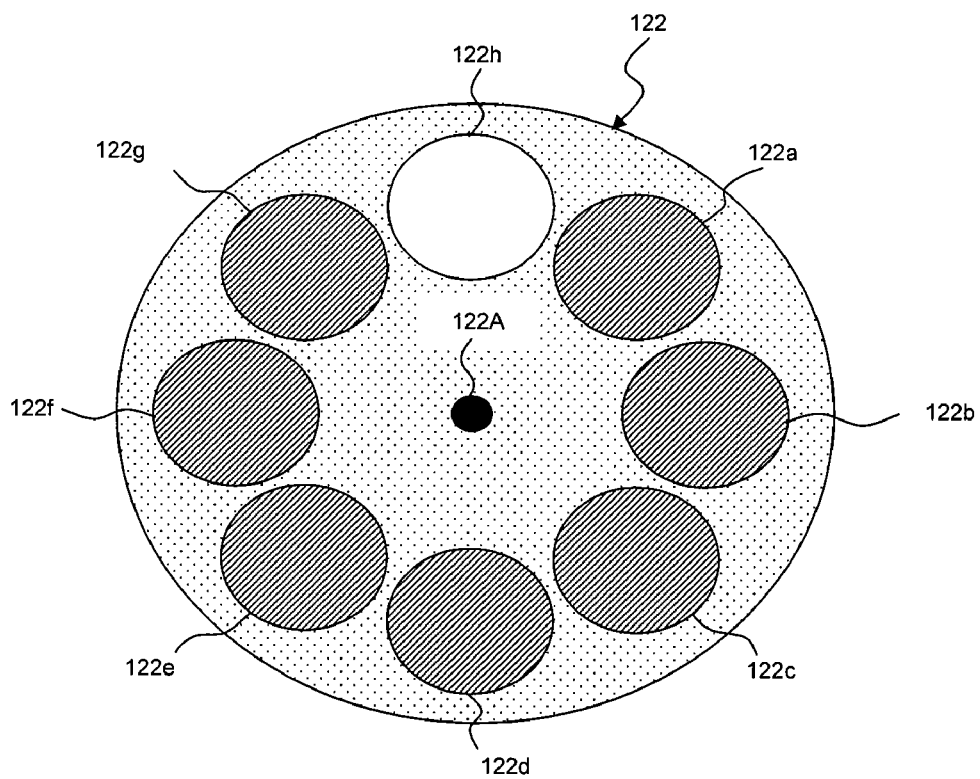
FIG. 5 is a schematic side view showing one example of the configuration of the optical system of the retinal camera of the preferred embodiment of the ophthalmologic imaging system according to the present invention.

The configuration of the retinal camera 1 will be described referring to FIGS. 1-5. FIG. 2 shows one example of the structural appearance of the retinal camera 1. FIGS. 3-5 show one example of the configuration of the optical system of the retinal camera 1.

As shown in FIG. 2, the retinal camera 1 has a platform 3 mounted on a base 2 so as to be slidable in the front and rear, right and left directions (horizontal direction). On the platform 3, an operation panel 3a and a control lever 4 are installed for the examiner to perform various operations.

An operator (examiner) operates the operation panel 3a when performing various operations of the retinal camera 1 and the ophthalmologic imaging system. The operation panel 3a is equivalent to one example of an "operation part" according to the present invention. The operation panel 3a includes a display 14 and an operation part 15 as shown in FIG. 1.

The display 14 displays various screens and information in accordance with control by a controller 11. This display 14 is composed of any display device such as an LCD (Liquid Crystal Display). The operation part 15 is provided with a button, key, and so on operated for performing various operations, such as operation of setting a view angle (imaging magnification), operation of setting an illumination light volume, and operation of selecting the subject.

The examiner can 3-dimensionally move the platform 3 mounted on the base 2 by operating the control lever 4. On the top of the control lever 4, an operation button 4a to be pressed down to capture a fundus oculi image is installed.

On the base 2, a post 5 is installed upright. On the post 5, a jaw rest 6a where the jaw of the subject is to be rested, a forehead pad 6b with which the forehead of the subject is brought into contact, and an external fixation lamp 7 emitting light for fixing an eye E are provided.

On the platform 3, a main body part 8 is installed to accommodate various optical systems and control systems of the retinal camera 1. The control system may be installed inside the base 2 or the platform 3, or in an external device such as the computer 30 connected to the retinal camera 1.

The side surface of the main body part 8 is provided with a filter change operation part 3b for switching a filter used in fundus oculi imaging. The filter change operation part 3b is equivalent to one example of an "operation part" according to the present invention.

The filter change operation part 3b is composed of, for example, a knob formed so as to be rotatable. When the filter change operation part 3b is rotated to a desired position, a desired one of a plurality of filters provided in filters 105 and 122 to be described later is arranged on a light path, depending on the position of the rotated filter change operation part. In addition, it is possible to retract all the filters from the light path, and it is also possible to arrange, on the light path, one filter of any of the filters 105 and 122 and at the same time to retract all the filters of the other one from the light path, by operating the filter change operation part 3b.

When the filter change operation part 3b is operated, a signal corresponding to the operation result is input to the controller 11. As a specific example, when the filter change operation part 3b is composed of the knob described above, an encoder for detecting the rotation position and inputting a signal to the controller 11 is provided on the filter change operation part 3b.

On the side of the eye E of the main body part 8 (the left side of the page of FIG. 2), an objective lens part 8a disposed so as to face the eye E is installed. Also, on the examiner's side of the main body part 8 (the right side of the page of FIG. 2), an eyepiece part 8b for observing the fundus oculi of the eye E with a naked eye is installed.

Further, the main body part 8 is provided with two imaging devices 9 and 10 for capturing images of the fundus oculi of the eye E. The imaging devices 9 and 10 are formed so as to be removable from the main body part 8, respectively.

The imaging devices 9 and 10 are digital cameras equipped with image pick-up elements 9a and 10a such as CCD (Charge Coupled Device) or CMOS (Complementary Metal Oxide Semiconductor). The imaging devices 9 and 10 transmit data (imaging signals) of captured images to the computer 30 through connection lines L1 and L2, respectively. The computer 30 performs processing such as displaying a captured image based on the imaging signals and compiling a database for storage. The imaging devices 9 and 10 function as one example of an "imaging part" according to the present invention.

The imaging devices 9 and 10 comprise image pick-up elements 9a and 10a for receiving lights of different wavelength regions, for example. In this embodiment, the image pick-up element 9a of the imaging device 9 would receive light of a visible region, and the image pick-up element 10a of the imaging device 10 would receive light of a visible region and infrared region.

In addition, the image pick-up element 9a of the imaging device 9 would be employed for color imaging, and the image pick-up element 10a of the imaging device 10 would be employed for monochrome imaging. The imaging device 9 is provided with a control circuit for changing imaging conditions such as imaging sensitivity (ISO sensitivity) and the film valid pixels of the image pick-up element 9a. On the other hand, the imaging device 10 is provided with a control circuit for changing imaging conditions such as imaging sensitivity (Gain) and the film valid pixels of the image pick-up element 10a.

This embodiment adopts a configuration in which two imaging devices are provided, but in the present invention, a configuration in which there is only one imaging device is also possible, and a configuration in which three or more imaging devices are provided is also possible, as long as a function corresponding to the imaging type is provided.

Configuration of Optical System of Retinal Camera

Next, referring to FIG. 3, a configuration of an optical system of the retinal camera 1 will be described. The optical system of the retinal camera 1 comprises an illumination optical system 100 configured to emit an illumination light to a fundus oculi Ef of the eye E, and an imaging optical system 120 configured to guide a fundus reflection light of the illumination light to the eyepiece part 8b and the imaging devices 9 and 10.

Illumination Optical System

The illumination optical system 100 comprises an observation light source 101, a condenser lens 102, an imaging light source 103, a condenser lens 104, a filter 105, a ring light-transmitting plate 107, a mirror 108, an LCD 109, an illumination diaphragm 110, a relay lens 111, an aperture mirror 112, and an objective lens 113.

The observation light source 101 is a light source that outputs a continuous light for observing the fundus oculi Ef with the naked eye or the captured image. This observation light source 101 is composed of, for example, a halogen lamp. The condenser lens 102 collects the light emitted from the observation light source 101 (observation illumination light) to form a parallel beam. Consequently, the observation illumination light illuminates the fundus oculi Ef almost evenly.

The imaging light source 103 is a light source that emits a flash to capture an image of the fundus oculi Ef. This imaging light source 103 is composed of, for example, a xenon lamp. The condenser lens 104 collects the flashed light from the imaging light source 103 (imaging illumination light) to form a parallel beam. Consequently, the imaging illumination light illuminates the fundus oculi Ef almost evenly.

The filter 105 comprises a plurality of optical filters selectively arranged on the light path of the illumination optical system 100. This filter 105 is composed of, as shown for example in FIG. 4, a circular disk (turret) on which a plurality of (seven) optical filters 105a-105g are positioned along the circumferential direction. Symbol 105h denotes a circular hole (or a transparent plate). A region of the filter 105 except the optical filters 105a-105h (for ease of description, the circular hole 105h may be referred to as the "optical filter") is not allowed to transmit light.

The filter 105 is rotatably held about a rotation axis 105A provided at the center position thereof. The rotation axis 105A is provided in a position off the light path of the illumination optical system 100. More specifically, the rotation axis 105A is positioned in a position such that optical filters 105a-105h are alternatively inserted into the light path when the filter 105 is rotated about the rotation axis 105A.

The optical filters 105a-105g provided on the filter 105 will be described. As the optical filters 105a-105g, a filter for color imaging, an exciter filter for FA (Fluorescein Angiography; visible fluorescence imaging), an exciter filter for ICG (IndoCyanine Green fluorescence angiography; infrared fluorescence imaging), an exciter filter for auto fluorescence, a filter for red-free imaging, and so on are employed. In addition to these filters, it is possible to employ any optical filter, depending on the particulars of the examination by the ophthalmologic imaging system.

The filter 105 rotates in conjunction with the operation for the filter change operation part 3b described above and works to switch the optical filter to be arranged on the light path. Herein, the aspect of the conjunction between the filter change operation part 3b and the filter 105 is optional. For example, the conjunction operation can be accomplished by a mechanical configuration in which a rotational operation for the filter change operation part 3b is transferred via a gear or the like to rotate the filter 105. In addition, the conjunction operation can also be accomplished by an electrical configuration that includes an encoder for detecting a rotational position of the filter change operation part 3b and a motor for rotating the filter 105 based on output signals from this encoder.

The ring light-transmitting plate 107 is a plate-like optical member having a ring light-transmitting part 107a composed of an annular light-transmitting region. This ring light-transmitting plate 107 is situated in a conjugate position with the pupil of the eye E, and situated so that the center of the ring light-transmitting part 107a is located on the optical axis of the illumination optical system 100. The mirror 108 reflects the illumination light emitted by the observation light source 101 or by the imaging light source 103, in the direction of the optical axis of the imaging optical system 120. The LCD 109 displays a fixation target (internal fixation target, not illustrated) for fixing the eye E.

The illumination diaphragm 110 is a diaphragm member shutting out part of the illumination light. This illumination diaphragm 110 is configured so as to be movable in the optical axis direction of the illumination optical system 100, thereby being capable of regulating an illumination region of the fundus oculi Ef. This illumination diaphragm 110 produces an effect such as prevention of occurrence of flare in a captured image.

The aperture mirror 112 is an optical element combining the optical axis of the illumination optical system 100 and the optical axis of the imaging optical system 120. In the center region of the aperture mirror 112, an aperture 112a is opened. The optical axis of the illumination optical system 100 and the optical axis of the imaging optical system 120 cross each other at a substantially central location of this aperture 112a. The objective lens 113 is installed in the objective lens part 8a of the main body part 8.

The illumination optical system 100 having such a configuration illuminates the fundus oculi Ef in the following manner. First, a case of observing the fundus oculi will be described. To begin with, the filter change operation part 3b is operated to position any of the optical filters 105a-105h on the light path, depending on the observation method. After that, observation illumination light is output from the observation light source 101. This observation illumination light is applied to the ring light-transmitting plate 107 through the condenser lenses 102 and 104. The light passed through the ring light-transmitting part 107a of the ring light-transmitting plate 107 is reflected by the mirror 108, and after passed through the LCD 109, the illumination diaphragm 110 and the relay lens 111, reflected by the aperture mirror 112. The observation illumination light reflected by the aperture mirror 112 advances in the optical axis direction of the imaging optical system 120, and is converged by the objective lens 113 to enter the eye E, thereby illuminating the fundus oculi Ef.

Since the ring light-transmitting plate 107 is placed in a conjugate position with the pupil of the eye E, a ring-shaped image of the observation illumination light entering the eye E is formed on the pupil at this moment. The fundus reflection light of the observation illumination light exits from the eye E through a central dark part of the ring-shaped image on the pupil. Thus, the illumination light entering the eye E and the fundus reflection light thereof are separated, whereby an influence of the observation illumination light entering the eye E on the fundus reflection light is prevented.

Next, a case of imaging the fundus oculi Ef will be described. To begin with, the filter change operation part 3b is operated to position any of the optical filters 105a-105h on the light path, depending on the imaging method. After that, the operation button 4a is pressed down, whereby imaging illumination light is flashed from the imaging light source 103. The imaging illumination light is applied to the fundus oculi Ef through a path similar to that of the observation illumination light.

Imaging Optical System

Next, the imaging optical system 120 will be described. The imaging optical system 120 comprises the objective lens 113, (the aperture 112a of) the aperture mirror 112, an imaging diaphragm 121, a filter 122, a focus lens 124, a magnifying lens 125, an imaging lens 126, a quick return mirror 127, and an imaging device 9.

The fundus reflection light of the illumination light exits from the eye E through the central dark part of the ring-shaped image on the pupil, as described above. The fundus reflection light having exited from the eye E enters the imaging diaphragm 121 through the aperture 112a of the aperture mirror 112. The aperture mirror 112 reflects the cornea reflection light of the illumination light, thereby preventing flare from occurring due to the cornea reflection light.

The imaging diaphragm 121 is a plate-shaped member having a plurality of circular light-transmitting parts of different sizes. The light-transmitting parts compose diaphragms with different diaphragm values (F values). These light-transmitting parts are selectively placed on the light path by a drive mechanism (not illustrated).

The filter 122 comprises a plurality of optical filters selectively arranged on the light path of imaging optical system 120. This filter 122 is composed of, as shown for example in FIG. 5, a turret on which a plurality of (seven) optical filters 122a-122g are positioned along the circumferential direction. Symbol 122h denotes a circular hole (or a transparent plate). A region of the filter 122 except the optical filters 122a-122h (symbol 122h may denote the "optical filter") is not allowed to transmit light.

The filter 122 is rotatably held about a rotation axis 122A provided on the center position thereof. The rotation axis 122A is set in a position off the light path of the imaging optical system 120, more specifically, in a position such that the optical filters 122a-122h are selectively inserted to the light path when the filter 122 rotates about the rotation axis 122A.

As the optical filters 122a-122g, for example, a filter for color imaging, a barrier filter for FA, a barrier filter for ICG, a barrier filter for auto fluorescence imaging, and so on are employed. Besides, it is possible to employ any optical filter, depending on the particulars of the examination by the ophthalmologic imaging system.

The filter 122 rotates in conjunction with the operation of the filter change operation part 3b described above, and works to switch the optical filter placed on the light path. The aspect of the conjunction between the filter change operation part 3b and the filter 122 is optional as in the case of the filter 122.

In this embodiment, in response to the operation of the filter change operation part 3b, both the filters 105 and 122 change the optical filter in conjunction with each other, but it is also possible to adopt a configuration in which a filter change operation part is provided for each of the filters 105 and 122.

In addition, as described later, in a case in which the optical filters 105a-105g and the optical filters 122a-122g are used in combination in this order, one optical filter may be a circular hole or a transparent plate. For example, one of the optical filters 105e and 122e used in combination may be a circular hole or a transparent plate that has no influence on transmission light. Instead of using a hole or transparent plate as one of the optical filters, it is also possible to control so as to use the other optical filter and the hole (transparent plate) 105h or hole (transparent plate) 122h in combination. For example, instead of using a hole or the like as the optical filter 122e, it is also possible to control so as to combine the optical filter 105e with the optical filter 122h.

The focus lens 124 can be moved in the optical axis direction of the imaging optical system 120 by a focus lens driving part 17 described later. This allows focusing during fundus oculi observation or fundus oculi imaging. In addition, the magnifying lens 125 is inserted to and retracted from the light path by a magnifying lens driving part 16 described later, and works to change the angle of view (magnification). In addition, the imaging lens 126 works to provide an image of the fundus reflection light from the eye E on the image pick-up element 9a of the imaging device 9.

The quick return mirror 127 is disposed rotatably around a rotary axis 127a by a drive mechanism not illustrated. In the case of imaging with the imaging device 9, the fundus reflection light is guided to the imaging device 9 by springing up the quick return mirror 127 obliquely mounted on the optical path. On the other hand, in the case of imaging with the imaging device 10 or observation of the fundus oculi with the naked eye of the examiner, the quick return mirror 127 is obliquely mounted on the light path to upwardly reflect the fundus reflection light.

The imaging optical system 120 is further provided with, for guiding the fundus reflection light reflected by the quick return mirror 127, a field lens 128, a switching mirror 129, an eyepiece 130, a relay lens 131, a reflection mirror 132, an imaging lens 133, and an imaging device 10.

The switching mirror 129 is rotatable around a rotary axis 129a, as well as the quick return mirror 127. This switching mirror 129 is obliquely disposed on the light path during observation of the fundus oculi with the naked eye, and reflects the fundus reflection light toward the eyepiece 130.

In the case of capture of a fundus oculi image by using the imaging device 10, the switching mirror 129 is retracted from the light path, and the fundus reflection light is guided toward the image pick-up element 10a. The fundus reflection light is passed through the relay lens 131, reflected by the mirror 132, and focused onto the image pick-up element 10a by the imaging lens 133.

Configuration of the Control System of the Retinal Camera

The configuration of the control system of the retinal camera 1 will be described referring to FIG. 1. The retinal camera 1 comprises a controller 11, a memory 12, a communication part 13 and a magnifying lens driving part 16, in addition to the aforementioned component parts. Hereinafter, the control system centered on these parts will be described.

Controller

The controller 11 controls the operation of each part of the retinal camera 1. In specific, the controller 11 performs control of ON/OFF switching of the observation light source 101 and the imaging light source 103, control of transmission/reception of data by the communication part 13, control of the operations of the magnifying lens driving part 16 and the focus lens driving part 17, and so on. In addition, the controller 11 controls the operation of setting the imaging sensitivity and the film valid pixels in each of the imaging devices 9 and 10. Moreover, the controller 11 performs control of the operation panel 3a, that is, control of a display operation by the display 14, or control of the operation of the retinal camera 1, depending on the operation of the operation part 15. In addition, the controller 11 stores information in the memory 12, and reads out the information stored in the memory 12. Moreover, the controller 11 performs various arithmetic processes, as needed.

The controller 11 comprises a microprocessor such as a CPU (Central Processing Unit). Furthermore, the controller 11 comprises a memory, such as a ROM (Read Only Memory) and a hard disk drive for storing a computer program for causing the microprocessor to perform the above operations.

Memory

The memory 12 stores various kinds of information for operations or processing by the retinal camera 1. The memory 12 is composed of a memory such as a RAM (Random Access Memory) or a hard disk drive.

Communication Part

The communication part 13 performs interactive data communication with the computer 30. As this communication part 13, a communication interface in conformity with any communication standard, such as a USB (Universal Serial Bus), may be employed. In FIG. 1, data communication in conformity with the USB or the like is performed through the connection line L. The connection lines L1 and L2 are cables for transmitting imaging signals output from the imaging devices 9 and 10 to the computer 30.

Magnifying Lens Driving Part

The magnifying lens driving part 16 is a drive mechanism for inserting and retracting the magnifying lens 125 to and from the light path of the imaging optical system 120. This magnifying lens driving part 16 comprises, for example, an actuator such as a motor for generating drive power and a transfer mechanism such as a gear for transferring the generated drive power to the magnifying lens 125. In addition, it is also possible to configure the magnifying lens driving part 16 by employing solenoid or the like.

Focus Lens Driving Part

The focus lens driving part 17 is a drive mechanism for moving the focus lens 124 along the optical axis direction of the imaging optical system 120. This focus lens driving part 17 comprises, for example, an actuator such as a motor for generating drive power and a transfer mechanism such as a gear for transferring the generated drive power to the focus lens 124.

Configuration of Computer

Figure 6:
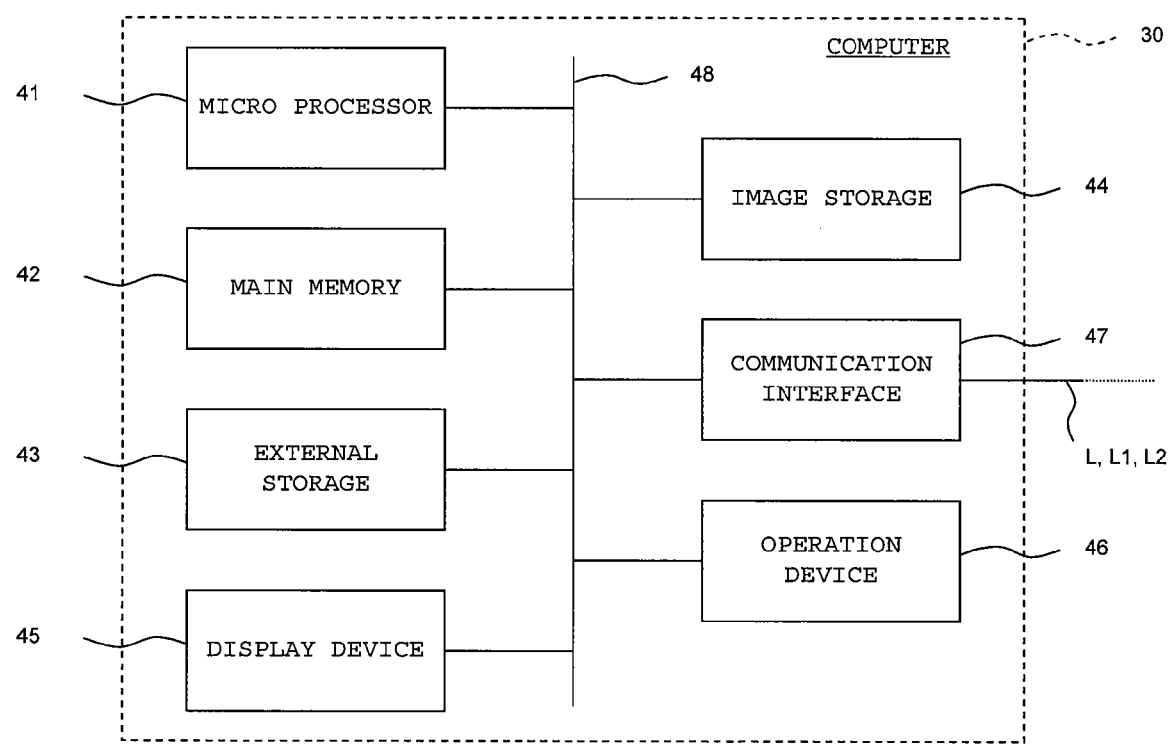
FIG. 6 is a schematic block diagram showing one example of the hardware configuration of a computer of the preferred embodiment of the ophthalmologic imaging system according to the present invention.

The configuration of the computer 30 will be described referring to FIGS. 1-6. FIG. 6 shows one example of the hardware configuration of the computer 30.

Hardware Configuration of Computer

The computer 30 comprises a microprocessor 41, a main memory 42, an external memory 43, an image memory 44, a display device 45, an operation device 46, and a communication interface 47. These parts 41-47 are connected to each other via a bus 48.

The microprocessor 41 comprises a CPU or the like, and performs various arithmetic processes and control processes related to the computer 30. The main memory 42 is composed of a RAM or the like. The external memory 43 is composed of a hard disk drive, a ROM and so on that stores various data and various computer programs for causing the microprocessor 41 to perform processes described later. The microprocessor 41 performs processes described later by loading, on the main memory 42, the data and computer programs stored in the external memory 43.

The image memory 44 stores image data of images captured with the imaging devices 9 and 10. In addition, the image memory 44 stores examination information of each subject. This examination information includes image data of the captured images, information on the setting status at imaging, and other medical chart information. The information is stored in a state searchable by means of identifying information of each subject (subject-identifying information such as patient ID and patient name).

This image memory 44 comprises a high-capacity memory such as a hard disk drive. In the example shown in FIG. 6, the external memory 43 and the image memory 44 are provided separately, but they may also be composed of a single hard disk drive or the like. In addition, the image memory 44 does not need to be built in the computer 30 but may also be composed of, for example, a server or a NAS (Network Attached Storage) that can be accessed by the computer 30.

The display device 45 is controlled by the microprocessor 41 to display various screens, images and so on. This display device 45 is composed of a display unit such as an LCD or a CRT (Cathode Ray Tube) display.

The operation device 46 is a device for inputting information for operating the computer 30 or retinal camera 1. This operation device 46 is composed of any input device (operation unit) such as a keyboard, mouse, trackball, joystick, and control panel.

In this embodiment, the display device 45 and the operation device 46 are separately described, but it is also possible to apply an instrument integrating a display function and an operation function, such as a touch-panel LCD or a pen tablet.

The communication interface 47 is a device for performing data communication via the connection lines L, L1 and L2. The communication interface 47 includes a communication interface in conformity with a communication standard such as a USB for data communication via the connection line L. Furthermore, the communication interface 47 includes a communication interface for receiving imaging signals from the imaging devices 9 and 10 through the connection lines L1 and L2.

In a case where the imaging devices 9 and 10 are directly controlled by the computer 30 (controlled without via the controller 11 of the retinal camera 1), the communication interface 47 comprises a communication interface for transmitting control signals via the connection lines L1 and L2.

The computer 30 may be connected to an information system in a medical institution. In this case, the communication interface 47 comprises a network interface or the like such as a LAN card. Moreover, it is also possible to provide a communication instrument such as a modem, thereby enabling wide-area communication such as the Internet communication.

Functional Configuration of Computer

The functional configuration of the computer 30 having the hardware configuration as described above will be described referring to FIG. 1. The computer 30 is provided with a controller 31, a display 33, an operation part 34, an image data memory 35, and a communication part 36. The controller 31 comprises an information memory 32.

Display, Operation Part, Image Data Memory, and Communication Part

First, the display 33, the operation part 34, the image data memory 35 and the communication part 36 will be described. The display 33 is composed of the display device 45 shown in FIG. 6. The display 33 is controlled by the controller 31 to display fundus oculi images based on imaging signals output from the imaging devices 9 and 10 and various information such as information on the setting of the retinal camera 1. The display 33 functions as one example of the "display" of the present invention.

The operation part 34 is composed of the operation device 46 shown in FIG. 6. Upon receiving an operation by a user, the operation part 34 inputs a signal corresponding to an operation content into the controller 31. Based on this signal, the controller 31 causes the computer 30 to perform an operation corresponding to that operation. The image data memory 35 functions as one example of the "memory" of the present invention, and is composed of the image memory 44 shown in FIG. 6. The communication part 36 is composed of the communication interface 47 shown in FIG. 6.

Controller

The controller 31 controls the operation of each part of the computer 30, and functions as one example of the "controller" of the present invention, together with the communication part 36. In addition, the controller 31 performs various arithmetic processes related to imaging by the retinal camera 1 and the captured image. The controller 31 comprises the microprocessor 41, the main memory 42, and the external memory 43, for example.

The controller 31 is provided with an information memory 32 composed of the main memory 42 and the external memory 43. The information memory 32 functions as one example of the "memory" according to the present invention, and previously stores, for example, information as shown in FIGS. 7-9. Herein, the information shown in FIGS. 7-9 is the equivalent of one example of the "relating information" according to the present invention.

Relating information 32a shown in FIG. 7 is information that associates the optical filters 105a-105h and 122a-122h of the filters 105 and 122 of the retinal camera 1, imaging types, and procedures. Herein, the imaging types indicate types of imaging methods and, as described above, include color imaging, FA imaging, ICG imaging, and so on. In addition, the procedure means the type of an imaging procedure (such as the imaging devices 9 or 10 to be used, or the setting status thereof) applied in the relevant imaging type.

In this embodiment, the optical filters of the two filters 105 and 122 would be used in the following combination: (1) the optical filters 105h and 122h (hole/transparent plate) are used at the time of color imaging; (2) the optical filters 105a and 122a are used at the time of FA imaging; (3) the optical filters 105b and 122b are used at the time of ICG imaging; (4) the optical filters 105c and 122c are used at the time of auto fluorescence imaging; (5) the optical filters 105d and 122d are used at the time of green imaging; and (6) the optical filters 105e and 122e are used at the time of blue imaging. In the case of applying this configuration, a hole or a transparent plate is employed as the optical filters 122d and 122e. In addition, although diagrammatic representation is omitted, the optical filters 105f and 122f and the optical filters 105g and 122g are respectively used, for example, in other imaging type such as red-free imaging.

In addition, "filter 8" in the relating information 32a shown in FIG. 7 indicates combination of the optical filters 105h and 122h, "filter 1" indicates combination of the optical filters 105a and 122a, "filter 2" indicates combination of the optical filters 105b and 122b, "filter 3" indicates combination of the optical filters 105c and 122c, "filter 4" indicates combination of the optical filters 105d and 122d, and "filter 5" indicates combination of the optical filters 105e and 122e (although not shown in FIG. 7, "filter 6" indicates combination of the optical filters 105f and 122f, and "filter 7" indicates combination of the optical filters 105g and 122g).

In the relating information 32a, the imaging type and the procedure are associated with (the combination of) the optical filters as follows: (1) the imaging type "color" and the procedure "for color" are associated with the filter 8; (2) the imaging type "FA" and the procedure "for B/W-1" are associated with the filter 1; (3) the imaging type "ICG" and the procedure "for B/W-2" are associated with the filter 2; (4) the imaging type "auto fluorescence" and the procedure "for B/W-2" are associated with the filter 3; (5) the imaging type "green" and the procedure "for B/W-1" are associated with the filter 4; and (6) the imaging type "blue" and the procedure "for B/W-1" are associated with the filter 5 (the following is omitted).

Herein, "B/W" means "Black/White", namely, monochrome imaging. In addition, "for B/W-1" and "for B/W-2" respectively mean the first procedure and the second procedure in monochrome imaging.

Next, relating information 32b shown in FIG. 8 will be described. In this relating information 32b, a procedure, one of the imaging devices 9 and 10, and a setting of the imaging device at imaging are associated. In other words, in the relating information 32b, the content of a procedure is associated with the name of the procedure.

More specifically, the relating information 32b defines associations as described below: (1) association of the imaging device "imaging device-A" and the setting "#1" with the procedure "for color"; (2) association of the imaging device "imaging device-B" and the setting "#1" with the procedure "for B/W-1"; and (3) association of the imaging device "imaging device-B" and the setting "#2" with the procedure "B/W-2" (the following is omitted).

Herein, the "imaging device-A" indicates the imaging device 9, and the "imaging device-B" indicates the imaging device 10. The information of "imaging device-A" and information of "imaging device-B" would be respectively predefined as identifying information of the imaging devices 9 and 10. This identifying information of the imaging device is the equivalent of one example of the "imaging setting information" according to the present invention. In addition, the settings "#1" and "#2" respectively indicate the first setting and the second setting in that imaging device.

Next, relating information 32c shown in FIG. 9 will be described. In this relating information 32c, an imaging device and setting thereof are associated with a content of the setting. The content of the setting is equivalent to one example of the "imaging setting information" according to the present invention, and include, for example, the imaging sensitivity and the film valid pixels of the imaging devices 9 and 10.

This relating information 32c defines associations as described below: (1) association of the imaging sensitivity "IS0500" and the film valid pixels "2000×1500" with the setting "imaging device-A, #1"; (2) association of the imaging sensitivity "Gain 12" and the film valid pixels "1600×1200" with the setting "imaging device-B, #1"; and (3) association of the imaging sensitivity "Gain 18" and the film valid pixels "1600×1200" with the setting "imaging device-B, #2" (the following is omitted).

Usage

Figure 10:
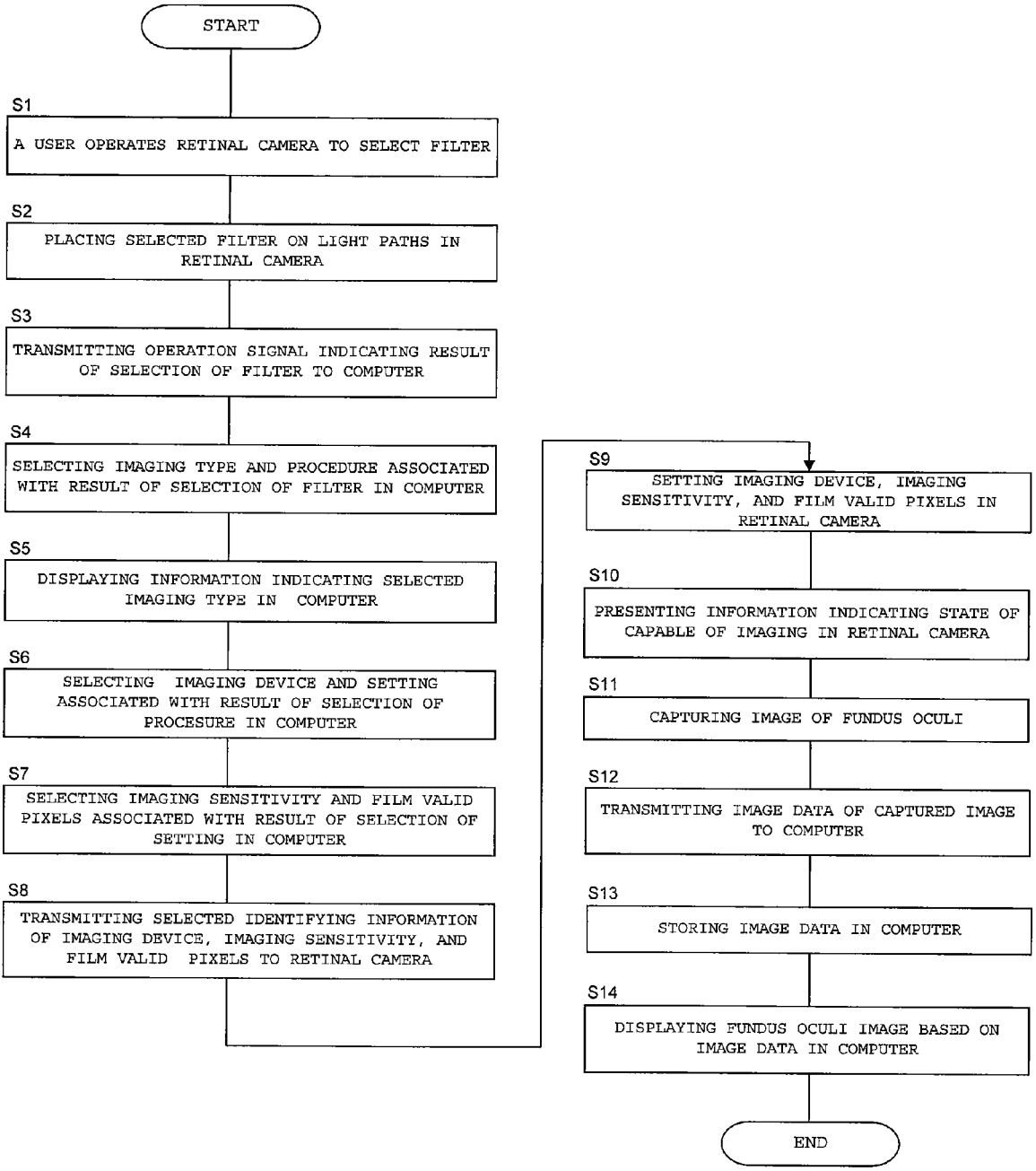
FIG. 10 is a flowchart showing one example of the usage in the preferred embodiment of the ophthalmologic imaging system according to the present invention.

A usage of the ophthalmologic imaging system having the aforementioned configuration will be described. A flowchart shown in FIG. 10 represents one example of the usage of the ophthalmologic imaging system.

An operation of the ophthalmologic imaging system according to selection of optical filters will be described referring to FIG. 10. To begin with, a user operates the filter change operation part 3b of the retinal camera 1 to select from among (the aforementioned combinations of) the optical filters 105a-105h and the optical filters 122a-122h (S1). The filters 105 and 122 are caused to place the selected optical filters on the respective light paths (S2).

In addition, the filter change operation part 3b inputs a signal corresponding to the result of the operation of step S1 into the controller 11. Based on this signal, the controller 11 generates a signal (operation signal) indicating the result of the operation, namely, the result of selection of the optical filter. Then, the communication part 13 is controlled to transmit this operation signal to the computer 30 via the connection line L (S3).

The operation signal transmitted from the retinal camera 1 is received by the communication part 36 of the computer 30, and input into the controller 31. The controller 31 refers to the relating information 32a stored in the information memory 32, and selects the imaging type and procedure associated with the result of selection of the optical filter represented by the operation signal (S4). The controller 31 causes the display 33 to display the name (abbreviation) of the selected imaging type, as information indicating the selected imaging type (imaging type information) (S5).

In addition, the controller 31 refers to the relating information 32b, and selects the imaging device and setting thereof corresponding to the procedure selected at step S4 (S6). Furthermore, the controller 31 refers to the relating information 32c, and selects the imaging sensitivity and film valid pixels corresponding to the selection result at step S6 (S7).

The controller 31 controls the communication part 36 to transmit the identifying information of the imaging device selected at step S6 and the information of the imaging sensitivity and film valid pixels selected at step S7, to the retinal camera 1 via the connection line L (S8).

The communication part 13 of the retinal camera 1 receives the identifying information of the imaging device, information of the imaging sensitivity and information of the film valid pixels transmitted from the computer 30, and inputs them into the controller 11. The controller 11 controls the imaging device 9 or imaging device 10 specified by this identifying information to set the imaging sensitivity and film valid pixels of the image pick-up element 9a or image pick-up element 10a, respectively (S9).

When the setting of the imaging device 9 or imaging device 10 is terminated, the controller 111 presents information indicating that it is in the state of capable of imaging (S10). For example, the controller 11 can cause the display 14 to display a message indicating the above. In addition, it is also possible to dispose a notifying light source such as an LED (Light Emitting Diode) to a predetermined site (e.g. the operation button 4a) of the retinal camera 1, and cause this notifying light source to light.

The user captures an image of the fundus oculi Ef by pressing the operation button 4a (S11). This image is obtained at the set imaging sensitivity and film valid pixels by the imaging device 9 or imaging device 10 set at step S9. The imaging device 9 or imaging device 10 transmits the image data of the captured image (the imaging signal) to the computer 30 via the connection line L1 or connection line L2 (S12).

When the communication part 36 of the computer 30 receives this image data, the controller 31 causes the image data memory 35 to store this image data (S13), and causes the display 33 to display a fundus oculi image based on this image data (S14). In the case of further capturing an image, the user will change the optical filter as desired, and repeat the processes of steps S1-S14. This is the end of the explanation of the operation of the ophthalmologic imaging system according to selection of optical filters.

Display Screen of Computer

Figure 11:
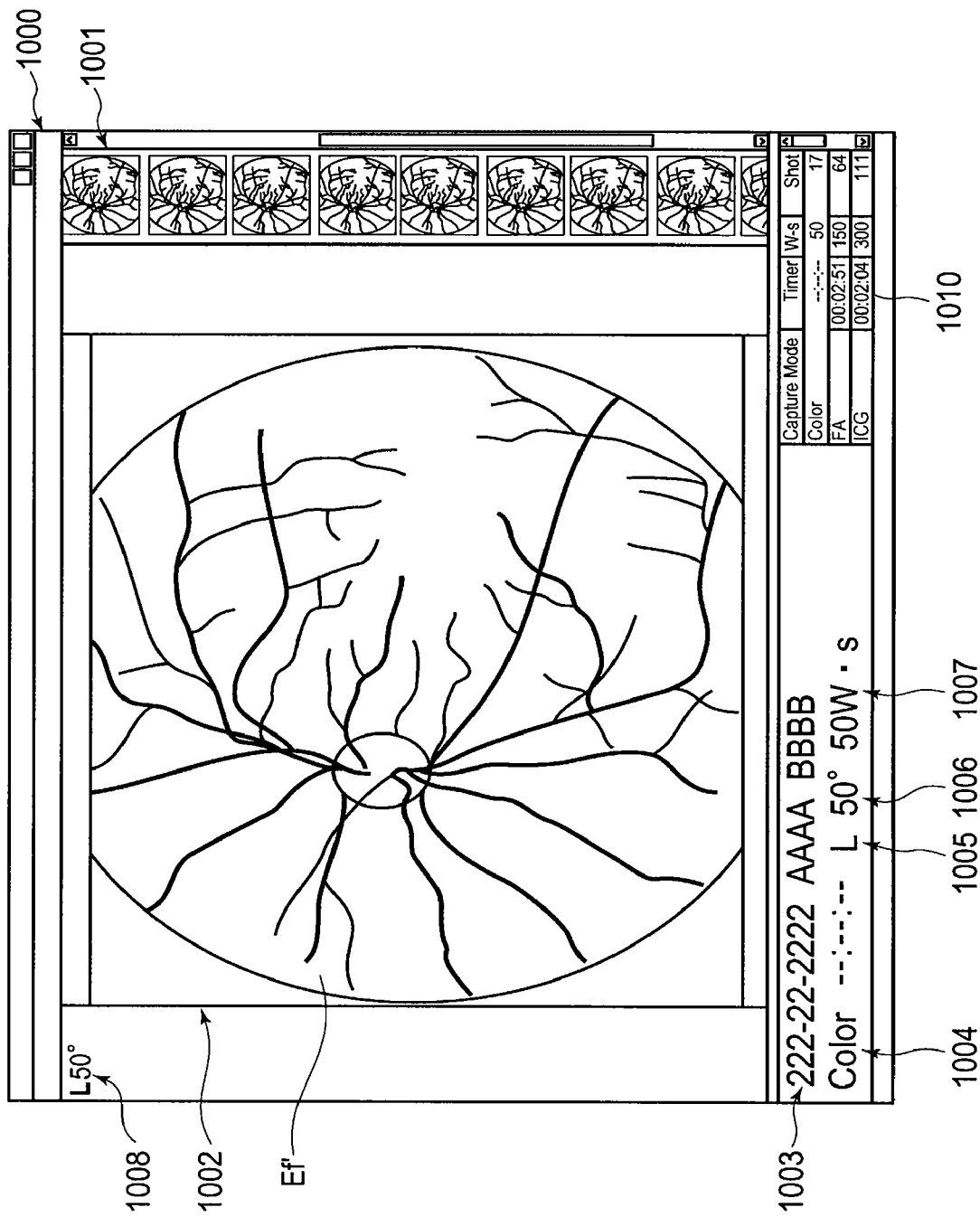
FIG. 11 is a schematic diagram showing one example of the screen displayed in the preferred embodiment of the ophthalmologic imaging system according to the present invention.

The display screen of the computer 30 in the above usage pattern will be described. FIG. 11 shows one example of this display screen. A display screen 1000 shown in FIG. 11 is a screen that displays a captured image of the fundus oculi Ef, a setting status at the time of imaging, and so on.

This display screen 1000 is provided with a thumbnail display 1001 and an image display 1002, as display regions for displaying a captured image. The thumbnail display 1001 displays reduced images (thumbnails) of a plurality of fundus oculi images in line. Image data of the fundus oculi images corresponding to these thumbnails is stored in the image data memory 35.

For the imaging types that are implemented while performing timing by means of a timer, such as FA imaging and ICG imaging, each thumbnail provided with timed time is displayed. The timed time when each fundus oculi image has been imaged is obtained by the timing function of the controller 11 (microprocessor) of the retinal camera 1. When the operation button 4a is pressed to capture an image, a signal is input from the operation button 4a to the controller 11. In response to input of this signal, the controller 11 causes the imaging light source 103 to flash and obtains the timed time of the timer and various types of information (information indicating the state of an optical filter, right and left eyes, imaging light volume, aperture values, angle of view, and so on). Then, the controller 11 attaches the above various types of information and identifying information to the information of the timed time, and transmits it to the computer 30. Furthermore, the imaging device 10 (9) transmits image data of the captured image (imaging signal) to the computer 30. The computer 30 associates the identifying information, the above various types of information and the timed time with the imaging signal. Then, the thumbnail based on the imaging signal is displayed with the timed time attached.

The user operates the operation part 34 to designate one of the thumbnails (e.g., clicks a desired thumbnail with the mouse). The controller 11 causes the image display 1002 to display, based on the image data corresponding to the designated thumbnail, the fundus oculi image Ef that is a magnified image of that thumbnail. Thus, the user can select and observe a desired one of the captured fundus oculi images.

Below the image display 1002, various types of information such as a current setting status are displayed. In specific, the display screen 1000 has a subject-identifying information display 1003, an imaging type display 1004, a L/R eye display 1005, a view angle display 1006, and an illumination light volume display 1007. In addition, the display screen 1000 has, on an upper left part thereof, an imaging information display 1008 for displaying information at the time of imaging.

Regarding Display of Subject-identifying Information

The subject-identifying information display 1003 displays identifying information of the subject (such as a patient ID and a patient name). In FIG. 11, a patient ID "222-22-2222" and a patient name "AAAA BBBB" are displayed.

The subject-identifying information is input when examination on the subject is started or when image observation is started (when observation of a previously captured image is started). For example, there are three cases of inputting the subject-identifying information as described below. A first one is a case in which a user operates the operation part 34 of the computer 30 to input. The first method includes a case of providing the computer 30 with a card reader, and inputting by reading, with the card reader, a patient card on which the subject-identifying information is stored by an electromagnetic method or the like.

A second one is a case in which, when examinations on a plurality of subjects are sequentially performed in a predetermined order, in response to a user's request for termination of the examination on one subject, the subject-identifying information of the next subject is automatically input. The computer 30 generally manages the examination order. When a request for termination of the examination is made on the retinal camera 1 side, the retinal camera 1 transmits a signal corresponding to this request to the computer 30. Upon reception of this signal, the computer 30 reads out and displays the subject-identifying information of the next subject.

A third one is a case in which the subject-identifying information is input on the retinal camera 1 side. In this case, the controller 11 of the retinal camera 1 causes the display 14 to display information for inputting the subject-identifying information. This information may be an input space into which a user manually inputs the subject-identifying information, or may be a list of the subject-identifying information. The user operates the operation part 15 to input desired subject-identifying information (or select it from the list). The retinal camera 1 transmits a signal indicating this input result (selection result) to the computer 30 via the connection line L. The computer 30 displays the input subject-identifying information based on this signal. In addition, the retinal camera 1 may have a card reader, thereby transmitting information indicating the reading result to the computer 30 via the connection line L and causing the computer 30 to display the information.

Input of the subject-identifying information as described above is performed when examination is started or when image observation is started. The controller 31 of the computer 30 reads out the examination information specified based on the input subject-identifying information (described above), from the image data memory 35. In a case where the information is input when examination is started, the past examination information of the subject is read out, for example. On the other hand, in a case where the information is input when image observation is started, the examination information including image data or the like of the image captured before is read out. The controller 31 executes control to display (part of) the read-out examination information. Consequently, for example, an imaging type, a fundus oculi image, a setting status at imaging, and so on are displayed on the display screen 1000. In addition, the current setting status of the retinal camera 1 may be obtained and displayed at the time of start of examination.

Regarding Display of Imaging Type

The imaging type display 1004 displays information on an imaging type (imaging type information) at step S5 of FIG. 10. That is, at step S4, the computer 30 obtains an imaging type corresponding to a selected optical filter from the relating information 32a and, at step S5, the computer 30 causes the imaging type display 1004 to display information indicating the obtained imaging type. Information displayed at this moment is the name or abbreviation of the imaging type, such as "Color" indicating color imaging, "FA" indicating visible fluorescence imaging, and "ICG" indicating infrared fluorescence imaging.

Regarding Display of L/R Eye

The L/R eye display 1005 displays information on whether the eye E to be imaged is the left eye or the right eye (referred to as L/R eye information).

A method for obtaining the L/R eye information will be described. As described above, the retinal camera 1 is provided with the jaw rest 6a and the forehead pad 6b. The subject puts his/her jaw on the jaw rest 6a and brings his/her forehead into contact with the forehead pad 6b, whereby the face position to the retinal camera 1 is fixed. In addition, the user slides the platform 3 in the front-rear and left-right directions on the base 2, thereby aligning the optical axis of the imaging optical system 120 of the retinal camera 1 to the left eye or the right eye of the subject (alignment).

The retinal camera 1 detects the position of the platform 3 on the base 2 (position in the left-right direction) and transmits the detection result to the computer 30 via the connection line L. The computer 30 receives this detection signal and determines whether the eye E is the left eye or the right eye based on the position in the left-right direction. Then, the computer 30 causes the L/R eye display 1005 to display the determination result. At this moment, for example, "L" is shown when the eye E is determined to be the left eye, and "R" is shown when the eye E is determined to be the right eye.

Regarding Display of View Angle

The view angle display 1006 displays the state (view angle) of the magnifying lens 125 of the retinal camera 1. A method for obtaining this view angle will be described. The view angle is set by the user operating the operation part 15 of the retinal camera 1 to make the magnifying lens driving part 16 work. The retinal camera 1 transmits this setting information of the view angle to the computer 30 via the connection line L. The computer 30 causes the view angle display 1006 to display the view angle indicated in this setting information. In FIG. 11, "50°" is displayed as the view angle.

Regarding Display of Illumination Light Volume

The illumination light volume display 1007 displays the illumination light volume (imaging light volume) set for the retinal camera 1. A method for obtaining this illumination light volume will be described. The illumination light volume is set by control of the imaging light source 103 by the controller 11 in response to an operation of the operation part 15 of the retinal camera 1. The retinal camera 1 transmits this setting information of the illumination light volume to the computer 30 via the connection line L. The computer 30 causes the illumination light volume display 1007 to display the illumination light volume indicated in this setting information. In FIG. 11, "50 W.s" is shown as the imaging light volume.

In the case of observation of the fundus oculi Ef with the observation light source 101 turned on, the illumination light volume of the observation light source 101 may be displayed on the illumination light volume display 1007, as is the case with the imaging light source 103.

Regarding Display of Imaging Information

The imaging information display 1008 displays various types of imaging information, such as the L/R eye information, the view angle, the timer, and the imaging light volume as shown in FIG. 11. This information is obtained by the aforementioned method.

Regarding Display of Imaging Type List

An imaging type list 1010 is displayed in a lower right position on the display screen 1000. This imaging type list 1010 is a list of imaging types (and imaging statuses thereof) that are currently practicable on the subject whose identifying information is displayed on the subject-identifying information display 1003. Typically, in ophthalmologic imaging, a plurality of imaging types may be concurrently implemented for one subject. For example, there is a case of, during intravenous injection of fluorescence agent for FA imaging (ICG imaging), performing FA imaging (ICG imaging) at a preferred timing and performing color imaging at a timing different from the FA and ICG imaging. In addition, color imaging, FA imaging, and ICG imaging may also be concurrently performed.

The above usage (refer to the flowchart in FIG. 10) is preferably employed in such concurrent imaging. In other words, for changing the imaging type on that subject (e.g., for changing from FA imaging to color imaging), the retinal camera 1 is brought into the setting status corresponding to a new imaging type, and the display screen of the computer 30 is also switched for the new imaging type, simply by changing the optical filter.

Now the imaging type list 1010 has display sections "Capture Mode," "Timer," "W.s," and "Shot." The display section "Capture Mode" displays an imaging type currently practicable on that subject. The display section "Timer" displays the timed time for imaging types that are performed with timing by a timer such as FA imaging and ICG imaging. The display section "W.s" displays the illumination light volume. The display section "Shot" displays the number of captured images.

The currently implemented imaging type is displayed in the imaging type list 1010 so as to be distinguishable from the imaging type in the imaging waiting state. For example, a method in which only the currently implemented imaging type is displayed inversely in black and white is applied.

The user can shift to a new imaging type by changing the optical filter as described above, and can additionally shift to a new imaging type also by designating a desired imaging type in the imaging type list 1010 by means of the operation part 15. In the latter case, imaging setting information (imaging device or setting) corresponding to the newly designated imaging type is obtained by referencing the relating information 32a through 32c in the FIG. 7 through FIG. 9 as is the case with the above usage, and the imaging setting information is transmitted to the retinal camera 1 to automatically perform setting.

Action and Effect

The action and effect of the aforementioned ophthalmologic imaging system will be described.

First, according to this ophthalmologic imaging system, in response to the filter change operation part 3b and the operation part 15 of the retinal camera 1 being operated, an operation signal is transmitted from the retinal camera 1 to the computer 30. The computer 30 works so as to display information on the display 33 based on this operation signal. Information displayed on the display 33 is, for example, imaging type information, imaging setting information, and so on.

According to the ophthalmologic imaging system working in this way, simply by operating the filter change operation part 3b or the operation part 15, information corresponding to that operation is displayed on the display 33. Therefore, it is not necessary to operate the computer 30 so as to display that information. Accordingly, it is possible to efficiently perform the imaging work with the retinal camera.

Furthermore, according to this ophthalmologic imaging system, it is possible to change the imaging type or the setting of the retinal camera 1 by operating the filter change operation part 3b or the operation part 15 of the retinal camera 1. Therefore, it is not necessary to operate the computer 30 for the changing operation. Accordingly, it is possible to efficiently perform the imaging work.

In addition, when shifting to fundus oculi imaging of a new subject, it is possible to perform the changing operation by the operation part 15 of the retinal camera 1, instead of performing the changing operation of the subject by the computer 30. Accordingly, it is possible to efficiently perform the imaging work.

In this embodiment, between the computer 30 and the retinal camera 1, various settings of the imaging devices 9 and 10 are communicated from the controller 31 of the computer 30 via the connection line L and passed through the controller 11 of the retinal camera 1, and image data is transmitted from the imaging devices 9 and 10 to the computer 30 via the connection lines L1 and L2. However, the communication of the various settings of the imaging devices 9 and 10 may be performed via the connection lines L1 and L2 that are directly connected to the imaging devices 9 and 10. Consequently, it is possible to change the imaging devices 9 and 10 to be used or to change the settings of the imaging devices 9 and 10 without making a change to the controller 11 of the retinal camera 1.

According to the above embodiment, in response to the operation part of the retinal camera being operated, the retinal camera transmits the operation signal to the computer, and the controller of the computer causes the display to display information based on the operation signal. Therefore, it is not necessary to operate the computer in order to display such information. Accordingly, it is possible to efficiently perform the imaging work with the retinal camera.

Modifications

The configuration described in detail above is merely one specific example of preferable implementation of the ophthalmologic imaging system according to the present invention. Therefore, it is possible to apply any modification as described below, for example.

Modification 1

In the above embodiment, as shown in the relating information 32a-32c in FIGS. 7-9, in response to designation of the optical filter, imaging setting information (the imaging device to be used or the setting thereof) is uniquely associated. However, the ophthalmologic imaging system according to the present invention is not limited to this.

For example, a case in which two or more imaging setting information are associated with a given optical filter will be described. First, the computer 30 transmits information indicating the two or more imaging setting information to the retinal camera 1. The information transmitted at this moment includes, for example, identifying information of two or more imaging devices, two or more imaging sensitivities, the film valid pixels, and so on.

The retinal camera 1 receives this information and causes the display 14 to display the two or more imaging setting information. The user operates the operation part 15 to designate a desired imaging setting status. The retinal camera 1 controls the imaging devices 9 and 10 to change each part of the retinal camera 1 to the designated setting. In addition, the retinal camera 1 transmits this designation result to the computer 30. The computer 30 causes the display 33 to display information based on the received designation result, as in the above embodiment.

According to such a modification, even when the image setting information is not uniquely associated with the optical filter, it is possible to change the imaging type or the setting of the retinal camera 1 simply by operating the retinal camera 1. Therefore, it is possible to efficiently perform imaging.

Modification 2

A case of concurrently performing two or more examinations of the imaging type using a timer will be described. This modification encompasses a case of concurrently performing imaging of different types, a case of concurrently performing imaging of the same type on two or more subjects, and a case of performing the above cases in combination.

Two or more types of imaging concurrently performed on a given subject are managed by the imaging type list 1010, as described in the above embodiment.

In addition, when the user performs a predetermined operation while concurrently examining two or more subjects, an examination management screen for managing these examinations is displayed on the display 33. When that operation is performed while another display screen such as the display screen 1000 shown in FIG. 11 is displayed, the examination management screen pops up (in other words, the examination management screen in a separate window from that display screen is displayed overlapping).

FIG. 12 shows one example of the examination management screen. Information on the respective examinations concurrently performed is listed on the examination management screen 2000 shown in FIG. 12. Specifically, the examination management screen 2000 contains display sections "ID," "First Name," "Last Name," "DB#," "Color," "FA," "ICG," "Green," "Blue," and "Auto F1."

The display section "ID" displays patient IDs of the respective subjects. The display section "First Name" displays first names of the respective subjects. The display section "Last Name" displays last names of the respective subject. The display section "DB#" displays identifying information of a database that keeps examination information of each examination. The display section "Color" displays presence or absence of performance of color imaging. The display section "FA" displays presence or absence of performance of FA imaging, and displays timed time of the timer, if FA imaging is performed. The display section "ICG" displays presence or absence of performance of ICG imaging, and displays timed time of the timer, if ICG imaging is performed. The display section "Green" displays presence or absence of performance of imaging using a green filter. The display section "Blue" displays presence or absence of performance of imaging using a blue filter. The display section "Auto F1" displays presence or absence of performance of auto fluorescence imaging, and displays timed time of the timer, if auto fluorescence imaging performed.

By employing the examination management screen 2000, it is possible to manage a plurality of examinations performed concurrently. For example, the display contents shown in FIG. 12 represent that examinations are concurrently performed on three subjects. In addition, it is possible to ascertain that FA imaging and ICG imaging are performed on a first subject (ID "222-22-2222") by viewing this examination management screen 2000. Furthermore, it is possible to ascertain that the timed time of FA imaging is 4 minutes and 40 seconds and that the timed time of ICG imaging is 3 minutes and 53 seconds. For another subject, it is also possible to ascertain the type of performed imaging and the elapsed time of the timer.

Although diagrammatic representation is omitted, the timed time of the timer related to the currently performed examination is displayed on the display 14 of the retinal camera 1. In addition, it is also possible to obtain the timed time of the currently performed examination by the timer of the computer 30, but it takes a few seconds to transmit an imaging signal from the retinal camera 1 to the computer 30, so that a difference may arise between the actual imaging timing and the timed time. Therefore, the timing related to the currently performed examination is preferably performed on the retinal camera 1 side.

Next, the timing aspect of the timer related to each imaging type will be described. Typically, in an ophthalmologic imaging system, the timer on the retinal camera side can time only a single time, and the timer on the computer side can concurrently time a plurality of times. In this modification, the timer of the computer 30 respectively performs timings related to a plurality of examinations displayed on the examination management screen 2000. On the other hand, the timer on the retinal camera 1 side performs only the timing related to one examination (currently performed examination) of these plural examinations. Hereinafter, specific examples of such processing will be described.

The computer 30 manages the timed time of examination of each imaging type (accompanying timing) for each subject. When one of the plural examinations that are concurrently performed is terminated, the user designates an examination to be performed next. Although this designation operation can be performed at the computer 30, it is desirable to be performed by the operation part 15 of the retinal camera 1. At this moment, the examination to be performed next may be designated from the list of examinations displayed on the display 14, or may be designated from the list displayed on the computer 30 side (examination management screen 2000) by operation of the operation part 15.

When a new examination is designated, the setting of the retinal camera 1 is changed to the setting corresponding to the imaging type of this new examination, as in the above embodiment.

In addition, in response to designation of the new examination the retinal camera 1 transmits the information indicating the designated examination to the computer 30. In a case where the designation operation has been performed on the side of the computer 30, this transmission process is not required. The computer 30 obtains the timed time related to the designated examination (indicated in the information from the retinal camera 1) and transmits it to the retinal camera 1. The timer of the retinal camera 1 starts the timing from this timed time.

By performing such a process, it is possible to obtain the timed time indicating the imaging timing of each image with high accuracy for each examination concurrently being performed.

Other Modification

An ophthalmologic imaging system including a retinal camera and a computer is described in the above embodiment. However, it is possible to apply the same configuration as in the above embodiment to an ophthalmologic imaging system including an ophthalmologic imaging device other than a retinal camera (such as a slit lamp or an OCT) and a computer.

What is claimed is:

1. An ophthalmologic imaging system comprising:
   a retinal camera having an illuminating optical system configured to project an illuminating light onto fundus oculi of a subject and an imaging optical system including an imaging part configured to receive the fundus reflection light of the illuminating light and output an imaging signal; and
   a computer having a package separate from the retinal camera, communicably connected to the retinal camera, and having a display configured to display a fundus oculi image based on the imaging signal, wherein:
   the retinal camera comprises an operation part;
   the computer comprises a controller configured to instruct the display to display information based on an operation signal transmitted from the retinal camera in response to an operation by the operation part;
   the illuminating optical system and/or the imaging optical system comprises an optical filter to be inserted onto a light path in response to an operation by the operation part; and
   based on the operation signal, the controller instructs the display to display imaging type information indicating an imaging type corresponding to the optical filter inserted onto the light path, as the information.

2. An ophthalmologic imaging system according to claim 1, wherein:
the illuminating optical system and/or the imaging optical system comprises a plurality of the optical filters to be selectively inserted onto the light path in response to the operation by the operation part; and
the controller comprises a memory that has pre-stored relating information in which an imaging type is related to each of the plurality of optical filters, selects an imaging type from the relating information based on the operation signal, and instructs the display to display the imaging type information indicating the imaging type.

3. An ophthalmologic imaging system according to claim 2, wherein:
the relating information associates each of the plurality of optical filters with imaging setting information indicating a setting status of the imaging part;
the controller selects the imaging setting information from the relating information based on the operation signal and transmits the imaging setting information to the retinal camera; and
the retinal camera changes the setting status of the imaging part based on the imaging setting information.

4. An ophthalmologic imaging system according to claim 3, wherein:
the imaging part includes two or more imaging devices;
the relating information associates identifying information of one imaging device of the two or more imaging devices as the imaging setting information with each of the plurality of optical filters; and
the retinal camera captures an image with the imaging device identified by the identifying information indicated in the imaging setting information.

5. An ophthalmologic imaging system according to claim 3, wherein:
the relating information associates imaging sensitivity and/or film valid pixels of the imaging part as the imaging setting information with each of the plurality of optical filters; and
the retinal camera changes the setting of the imaging part to the imaging sensitivity and/or film valid pixels indicated in the imaging setting information, and captures an image.

6. An ophthalmologic imaging system according to claim 1, wherein:
when setting of imaging view angle, setting of light volume of the illuminating light, or setting of L/R eye are directed via the operation part, the retinal camera transmits a operation signal including information of the setting; and the controller instructs the display to display, based on information of the setting included in that operation signal, the information indicating the view angle, light volume of the illuminating light, or the L/R eye set by the operation part.

7. An ophthalmologic imaging system according to claim 1, wherein:
the retinal camera is capable of displaying subject-identifying information and, when the displayed subject-identifying information is changed via the operation part, transmits an operation signal including the subject-identifying information having been changed; and
the controller comprises a memory for storing examination information on each of a plurality of subjects to be examined, selects examination information from the memory based on the subject-identifying information included in the operation signal, and instructs the display to display the examination information.

\* \* \* \* \*